(12) United States Patent
Xu

(10) Patent No.: US 6,410,244 B1
(45) Date of Patent: Jun. 25, 2002

(54) METHOD FOR PREPARING PLASMIDS, AND USES RELATED THERETO

(75) Inventor: Hong Wu Xu, Lexington, MA (US)

(73) Assignee: Curis, Inc., Cambridge, MA (US)

( * ) Notice: Subject to any disclaimer, the term of this patent is extended or adjusted under 35 U.S.C. 154(b) by 0 days.

(21) Appl. No.: 09/704,230

(22) Filed: Nov. 1, 2000

Related U.S. Application Data

(60) Provisional application No. 60/162,993, filed on Nov. 1, 1999.

(51) Int. Cl.⁷ .............................. C12Q 1/68; C12Q 1/02; C12N 15/63; C12N 1/02; C12N 1/21
(52) U.S. Cl. ..................... 435/6; 435/243; 435/252.3; 435/254.11; 435/320.1; 435/7.1; 435/30; 435/252.1; 435/261
(58) Field of Search .............................. 435/243, 252.3, 435/254.11, 320.1, 6, 7.1, 30, 252.1, 261

(56) References Cited

U.S. PATENT DOCUMENTS 5,654,150 A  *  8/1997  King et al. ..................... 435/6

OTHER PUBLICATIONS

Hanahan et al., 1991, "Plasmid transformation of *Escherichia coli* and other bacteria", Meth. Enzymol. 204:63–113.

* cited by examiner

*Primary Examiner*—David Guzo
(74) *Attorney, Agent, or Firm*—Ropes & Gray; Matthew P. Vincent; David P. Halstead

(57) ABSTRACT

The invention relates to methods of preparing plasmid pools by growing colonies in discrete wells of a semi-solid or gelatinous medium. This method may facilitate colony collection, reduce colony overgrowth, reduce contamination by adventitious microorganisms, and increase the efficiency of plasmid screening techniques.

8 Claims, No Drawings

METHOD FOR PREPARING PLASMIDS, AND USES RELATED THERETO

RELATED APPLICATION

This application is a continuation of U.S. Provisional Application No. 60/162,993, filed Nov. 1, 1999, the entire contents of which are hereby incorporated by reference.

FIELD OF THE INVENTION

The invention relates to a method for preparing plasmids, particularly a method amenable for use with high-throughput library screening.

BACKGROUND OF THE INVENTION

Current processes for producing plasmids for screening generally involve plating a large number of colonies, culturing the colonies, and scraping the colonies into microtubes for analysis. This process, however, can be labor intensive, because a researcher must manually transfer colonies to the microtubes. Furthermore, the scraping process may break cells, resulting in a viscous solution, and also creates a substantial risk of contamination from adventitious microorganisms. Thus, this process limits the rate and reliability of gene expression library screening. A convenient and simple method for preparing a plasmid pool suitable for high-throughput screening would substantially increase productivity and efficiency of the screening process.

SUMMARY OF THE INVENTION

The present invention generally relates to a method for culturing a plasmid library by combining a plasmid library comprising a plurality of microorganisms, each transfected with one of a plurality of plasmids or other nucleic acid constructs, with a semi-solid or gelled culture medium, dividing the culture medium between at least ten receptacles (e.g., wells), incubating the receptacles, and separating the microorganisms from the culture medium. In certain embodiments, the method includes isolating DNA from the microorganisms.

DETAILED DESCRIPTION OF THE INVENTION

The present invention relates to a method of preparing plasmids wherein a plasmid library, e.g., a variegated library of genetic constructs (plasmids, vectors, etc.), is mixed with a culture medium which is then divided among a plurality of reservoirs. The culture medium is preferably a semi-solid matrix, e.g., a polymer gel, such as agar, agarose, gelatin, methylcellulose, etc. After culturing, the cells may be separated from the culture medium, e.g., by centrifugation or filtration, and the plasmids may be prepared by techniques known in the art. Because the individual cultures are separate from each other, preferably in a predefined arrangement, the final preparation process may be automated, e.g., by using a robot.

I. Definitions

Before further description of the preferred embodiments of the subject invention, certain terms employed in the specification, examples, and appended claims are collected here for convenience. "Culture medium" refers to a liquid, semi-solid, or solid solution including sufficient nutrients for supporting the growth of microorganisms.

The terms "gel" and "semi-solid" are used herein to refer to a material, such as a polymer or other crosslinked (e.g., covalently or non-covalently) matrix, in which the diffusion of particles, such as microorganisms, is substantially impeded relative to in a liquid.

"Gelling agent" refers to a compound which can be added to a liquid to thicken liquid, for example, to provide a solid or semi-solid material, such as a gel. Common gelling agents include agar and agarose.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides. ESTs, chromosomes, cDNAs, mRNAs, and rRNAs are representative examples of molecules that may be referred to as nucleic acids.

The term "plasmids" refers generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

A "plasmid library" or "expression library," as the terms are used herein, refers to variegated library of transformed cells, e.g., a plurality of microorganisms each expressing a plasmid, wherein a plurality of different plasmids, e.g., at least 10, preferably at least 100, even more preferably at least 1000, 10,000, or more, are represented in the plurality of microorganisms.

"Selection agent" refers to a compound added to a culture medium which inhibits the growth of microorganisms which lack a particular gene. For example, ampicillin is a selection agent which inhibits the growth of microorganisms which lack an ampicillin resistance gene.

"Recovery" or "isolation" of a given DNA means separation of the DNA from a host cell.

The terms "replicable expression vector" and "expression vector" refer to a piece of nucleic acid, e.g., DNA (usually double-stranded), which may have inserted into it a piece of foreign DNA. Foreign DNA is defined as heterologous DNA, which is DNA not naturally found in the host cell. The vector is used to transport the foreign or heterologous DNA into a suitable host cell. Once in the host cell, the vector can replicate independently of the host chromosomal DNA, and several copies of the vector and its insert (foreign) DNA may be generated. In addition, the vector may, if appropriate, contain the necessary elements that permit translating the foreign DNA into a polypeptide.

The terms "transformed host cell" and "transformed" refer to the introduction of DNA or other nucleic acids into a cell. The cell is termed a "host cell", e.g., a prokaryotic cell. Typical prokaryotic host cells include various strains of E. coli. The introduced DNA is usually in the form of a vector containing an inserted piece of DNA. The introduced DNA is usually in the form of a vector containing an inserted piece of DNA. The introduced DNA sequence may be from the same species as the host cell or a different species from the host cell, or it may be a hybrid DNA sequence, containing some foreign and some homologous DNA.

II. Methods of the Present Invention

The present invention generally relates to methods for preparing libraries of nucleic acid constructs by amplifications using transfected microorganisms. Generally, microorganisms of an expression library are added to culture medium to which a gelling agent and, optionally, a selection agent is added. Preferably, the concentration of microorganisms in the culture medium is between 1 and 1000 colony-forming units (CFU) per mL, more preferably between 10 and 500 cfu/mL, and even more preferably between 50 and 400 cfu/mL. The culture medium is then divided among a plurality of reservoirs, such as wells, test tubes, vials, or other suitable containers. The culture medium containing the microorganisms is then incubated and cultured according to techniques well known in the art. The resulting colonies of microorganisms may then be separated from the growth medium, e.g., by centrifugation, filtration, or other suitable means. The resulting cells may then be processed to prepare the plasmids, e.g., by lysing the cells, purifying the plasmid DNA, etc. The processing may be automated, e.g., by using a robot.

Dividing the growth medium among a plurality of reservoirs has several advantages. For example, using standard plating techniques, colonies of cells may be overgrown and/or crowded out by neighboring colonies. Elimination of colonies in this fashion skews the proportions of plasmids detected, potentially affecting the outcome of the experiment. Using separated reservoirs, however, overgrowth is substantially curtailed, preserving the representation of plasmids in the original population of microorganisms. The use of a semi-solid or gelled matrix further hampers overgrowth, because each colony is relatively isolated in three-dimensional space, restricting the possibility of overgrowth into a neighboring colony. Additionally, using standard plating techniques, the colonies must be removed from the plate by hand and transferred into receptacles for further processing. Using the method of the present invention, the colonies are already divided into individual receptacles, obviating the need for this step. Furthermore, by employing a plurality of receptables arranged in a predetermined array, much of the processing may be automated, e.g., by employing robotic manipulation of the samples. This procedure has the added advantage that the entirety of the medium is harvested for cells, unlike the traditional scraping method which potentially may overlook and fail to harvest some colonies.

General techniques for culturing or growing microorganisms containing plasmids are well known in the art, for example, as described in Sambrook, J., Fritsch, E. F. & Maniatis, T. (1989) Molecular cloning: a laboratory manual (Cold Spring Harbor Laboratory, Cold Spring Harbor, N.Y.) and may readily be adapted for use in the methods of the present invention. Typically, the microorganisms are cultured using a liquid medium such as LB (Luria-Bertani), NZYCM, Terrific Broth, SOB, SOC, 2xYT, M9 Minimal media, other media known in the art, or variations thereof to which a gelling agent such as agar or agarose is then added to the culture medium to thicken or solidify the medium. Additional suitable gelling agents include isolated carbohydrates such as corn starch, potato starch, wheat starch, rice starch, cellulose, pectin, and gums; bioavailable sugars such as glucose, fructose, and sucrose; chemically modified starches such as modified corn starch, methylcellulose, carboxymethylcellulose, and dextrin. A preferred gelling agent is SeaPrep agarose, which melts below 50° C. A variety of culture media, gelling agents, and ingredients therefor are commercially available, e.g., from Sigma, Bacto, and Difco, and may be used in the methods described herein without departing from the scope and spirit of the invention. Semi-solid growth conditions in 3-D are further discussed in Kriegler, M. "Gene Transfer and Expression: A Laboratory Manual" Stockton Press, N.Y., 1990, pp. 131–132 and Hanahan, D. et al., *Methods Enzymol.*, 1991, 204, 63–113.

Nutrients such as nitrogen sources, inorganic salts and growth-promoting substances may be added to the culture medium depending upon the type of the microorganism to be cultured. Nitrogen sources which may be included in the culture medium include, for example, ammonium salts such as ammonium sulfate, ammonium chloride, ammonium nitrate and ammonium phosphate, nitric acid salts such as potassium nitrate, sodium nitrate and ammonium nitrate; organic nitrogen such as glutamic acid, glutamine, aspartic acid and asparagine; and ammonia, to be used either alone or in combination. Examples of inorganic salts are potassium monohydrogen phosphate, potassium dihydrogen phosphate, magnesium sulfate, iron sulfate, and manganese sulfate either alone or in combination. There is no particular restriction on the growth promoter substances, and examples that can be cited are vitamins such as thiamin and biotin, amino acids such as methionine and cysteine, and substances wholly or partly containing vitamins or amino acids, such as yeast extract, polypeptone, meat extract, corn steep liquor and Casamino acid.

There is no limitation on the contents of these nutrients in the culture medium, and may be those contents which are used in ordinary cultivations. The nutrients derived from natural materials are suitably contained in amounts of usually 1 to 0.1%, preferably 0.5 to 0.2%, in the culture medium.

Furthermore, in embodiments wherein the microorganisms being cultured include a marker gene, such as an antibiotic resistance gene, the culture medium may be designed to select for that marker, such as by adding an antibiotic, thereby reducing contamination by unwanted microorganisms from the environment.

The cultivation of the microorganism in the culture medium having the above composition may be carried out under aerobic conditions by using the same cultivation device as used normally. The cultivation conditions may be selected so as to be suitable for the type of the transformed microorganism. Generally, the cultivation temperature is about 10 to about 45° C., preferably about 25 to about 40° C., and the pH of the culture medium may be maintained at about 3 to 10, preferably about 5 to 9. Where the pH of the culture medium varies during the cultivation, bases such as ammonia, sodium hydroxide, potassium hydroxide, sodium carbonate and sodium hydrogen carbonate, or acids such as sulfuric acid and hydrochloric acid are desirably added to adjust the pH. The cultivation time may be adjusted usually to about 5 to 48 hours.

IV. Exemplification

The invention now being generally described, it will be more readily understood by reference to the following example which is included merely for purposes of illustration of certain aspects and embodiments of the present invention, and is not intended to limit the invention.

In one practice, the method of the present invention may be carried out as follows:

1) 0.36 g SeaPrep agarose is combined with 120 mL of 2xLB medium in an autoclavable bottle.
2) The bottle is autoclaved for 30 min.
3) The bottle is cooled to 37° C. in a water bath for at least an hour.

4) 120 µL of ampicillin (100 mg/mL) is added to the medium.

5) 3.6×10⁴ cfu of an expression library are mixed with the broth.

6) 1 mL medium is added to each well of a 96-well plate.

7) 1 mL medium is added to a Falcon 2057 tube (control).

8) 100 µL medium is added to an Ampicillin/LB plate (control).

9) The plate is incubated for 1 h in an ice water bath. The water level should reach or exceed the level of the medium.

10) The plate is incubated at 30° C. for 45 h.

11) The plate is warmed up to 50° C. to completely melt the semi-solid medium before centrifugation.

12) The plate is centrifuged at 37° C. at 1,700 g for at least 40 min.

13) The semi-solid agarose supernatant is decanted.

14) The remaining cell pellets are subsected to plasmid preparation according to manufacturer's instructions, e.g., for BIO ROBOT 9600 from Qiagen, the manual of which is hereby incorporated by reference.

It was observed that adding 2% glycerol in the semi-solid 2×LB media could increase the yield of plasmid.

SeaPrep agarose is an ultra-low gelling temperature agarose with a melting temperature (for 1% preparations) lower than 50° C. Therefore, shifting the temperature from 30° C. to 50° C. to liquify the semi-solid media before centrifuging may further increase the yield of plasmid.

The controls may be utilized to verify a suitable experiment. For example, colony growth should be observed throughout the medium in the Falcon tube after incubation. Also, the number of colonies on the ampicillin plate should be approximately 30.

The DNA concentration provided by this experiment is around 20 ng/µL, yielding approximately 1.5 µg overall.

All of the references and publications cited herein are hereby incorporated by reference.

EQUIVALENTS

Those skilled in the art will recognize, or be able to ascertain using no more than routine experimentation, numerous equivalents to the methods described herein. Such equivalents are considered to be within the scope of this invention and are covered by the following claims.

I claim:

1. A method for culturing a plasmid library, comprising
   combining a plasmid library comprising a plurality of microorganisms, each expressing one of a plurality of plasmids, with a culture medium comprising a gelling agent,
   dividing the culture medium between at least ten receptacles,
   incubating the receptacles, and
   separating the microorganisms from the culture medium.

2. The method of claim 1, further comprising isolating DNA from the microorganisms.

3. The method of claim 1, wherein the culture medium comprises a selection agent.

4. The method of claim 1, wherein the gelling agent is selected from agar or agarose.

5. A method for culturing a plasmid library, comprising
   combining a plasmid library comprising a plurality of microorganisms, each expressing one of a plurality of plasmids, with a culture medium,
   adding a gelling agent to the culture medium,
   dividing the culture medium between at least ten receptacles,
   incubating the receptacles, and
   separating the microorganisms from the culture medium.

6. The method of claim 5, further comprising isolating DNA from the microorganisms.

7. The method of claim 5, wherein the culture medium comprises a selection agent.

8. The method of claim 5, wherein the gelling agent is selected from agar or agarose.

* * * * *